US012484906B2

(12) United States Patent
Solaun et al.

(10) Patent No.: US 12,484,906 B2
(45) Date of Patent: *Dec. 2, 2025

(54) HOOK WIRE FOR PREVENTING PREMATURE EMBOLIC IMPLANT DETACHMENT

(71) Applicant: DePuy Synthes Products, Inc., Raynham, MA (US)

(72) Inventors: Daniel Solaun, Miami, FL (US); David Blumenstyk, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/431,353

(22) Filed: Feb. 2, 2024

(65) Prior Publication Data

US 2024/0173031 A1 May 30, 2024

Related U.S. Application Data

(63) Continuation of application No. 17/685,147, filed on Mar. 2, 2022, now Pat. No. 11,937,825.

(51) Int. Cl.
*A61B 17/12* (2006.01)
*A61B 17/00* (2006.01)

(52) U.S. Cl.
CPC .. *A61B 17/12113* (2013.01); *A61B 17/12145* (2013.01); *A61B 2017/12054* (2013.01)

(58) Field of Classification Search
CPC ........ A61B 17/12113; A61B 17/12145; A61B 17/12031; A61B 17/1214; A61B 17/12022; A61B 17/12131; A61B 17/12177; A61B 2017/12054; A61B 2017/12172; A61F 2/011; A61F 2/9517; A61F 2002/9505; A61F 2002/9511
See application file for complete search history.

(56) References Cited

U.S. PATENT DOCUMENTS 2,220,203 A 11/1940 Branin
3,429,408 A 2/1969 Maker et al.
(Continued)

FOREIGN PATENT DOCUMENTS

CN 102125451 A 7/2011
CN 103356260 A 10/2013
(Continued)

*Primary Examiner* — Tan-Uyen T Ho
*Assistant Examiner* — Lindsey R. Rivers
(74) *Attorney, Agent, or Firm* — Troutman Pepper Locke LLP

(57) ABSTRACT

Various systems and methods of delivering an implant to a target location of a body vessel are disclosed. A detachment system can include a tubular body including a lumen extending therethrough and a distal tube on a distal end of the tubular body. A loop wire can be affixed at a first end to the tubular body and can include a loop opening positioned approximate a distal end of the distal tube. A pull wire can extend through the lumen. A hook wire can extend radially through a sidewall of the distal tube and into the lumen. The hook wire can be positioned around a pull wire portion and tensioned such that the pull wire portion abuts the distal tube and provides frictional resistance between the pull wire portion and the sidewall of the distal tube. The frictional resistance can be effective to inhibit premature detachment of the implant.

20 Claims, 5 Drawing Sheets

(56) References Cited

U.S. PATENT DOCUMENTS

| | | | |
|---|---|---|---|
| 4,858,810 | A | 8/1989 | Intlekofer et al. |
| 5,069,674 | A | 12/1991 | Fearnot et al. |
| 5,108,407 | A | 4/1992 | Geremia et al. |
| 5,122,136 | A | 6/1992 | Guglielmi et al. |
| D329,698 | S | 9/1992 | Loney et al. |
| 5,234,437 | A | 8/1993 | Sepetka |
| 5,250,071 | A | 10/1993 | Palermo |
| 5,263,964 | A | 11/1993 | Purdy |
| 5,334,210 | A | 8/1994 | Gianturco |
| 5,350,397 | A | 9/1994 | Palermo et al. |
| 5,382,259 | A | 1/1995 | Phelps et al. |
| 5,392,791 | A | 2/1995 | Nyman |
| 5,484,409 | A | 1/1996 | Atkinson et al. |
| 5,536,248 | A | 7/1996 | Weaver et al. |
| 5,569,221 | A | 10/1996 | Houser et al. |
| 5,645,558 | A | 7/1997 | Horton |
| 5,899,935 | A | 5/1999 | Ding |
| 5,925,059 | A | 7/1999 | Palermo et al. |
| 6,113,622 | A | 9/2000 | Hieshima |
| 6,203,547 | B1 | 3/2001 | Nguyen et al. |
| 6,391,037 | B1 | 5/2002 | Greenhalgh |
| 6,454,780 | B1 | 9/2002 | Wallace |
| 6,506,204 | B2 | 1/2003 | Mazzocchi |
| 6,561,988 | B1 | 5/2003 | Turturro et al. |
| 7,367,987 | B2 | 5/2008 | Balgobin et al. |
| 7,371,251 | B2 | 5/2008 | Mitelberg et al. |
| 7,371,252 | B2 | 5/2008 | Balgobin et al. |
| 7,377,932 | B2 | 5/2008 | Mitelberg et al. |
| 7,384,407 | B2 | 6/2008 | Rodriguez et al. |
| 7,708,754 | B2 | 5/2010 | Balgobin et al. |
| 7,708,755 | B2 | 5/2010 | Davis, III et al. |
| 7,799,052 | B2 | 9/2010 | Balgobin et al. |
| 7,811,305 | B2 | 10/2010 | Balgobin et al. |
| 7,819,891 | B2 | 10/2010 | Balgobin et al. |
| 7,819,892 | B2 | 10/2010 | Balgobin et al. |
| 7,901,444 | B2 | 3/2011 | Slazas |
| 7,985,238 | B2 | 7/2011 | Balgobin et al. |
| 8,062,325 | B2 | 11/2011 | Mitelberg et al. |
| 8,333,796 | B2 | 12/2012 | Tompkins et al. |
| 8,926,650 | B2 | 1/2015 | Que et al. |
| 8,956,381 | B2 | 2/2015 | Que et al. |
| 9,155,540 | B2 | 10/2015 | Lorenzo |
| 9,232,992 | B2 | 1/2016 | Heidner |
| 9,314,326 | B2 | 4/2016 | Wallace et al. |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,120 | B2 | 5/2017 | Lagodzki et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Paterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 9,918,718 | B2 | 3/2018 | Lorenzo |
| 10,149,676 | B2 | 12/2018 | Mirigian et al. |
| 10,285,710 | B2 | 5/2019 | Lorenzo et al. |
| 10,292,851 | B2 | 5/2019 | Gorochow |
| 10,420,563 | B2 | 9/2019 | Hebert et al. |
| 10,517,604 | B2 | 12/2019 | Bowman et al. |
| 10,668,258 | B1 | 6/2020 | Calhoun et al. |
| 10,806,402 | B2 | 10/2020 | Cadieu et al. |
| 10,806,461 | B2 | 10/2020 | Lorenzo |
| 11,951,026 | B2 | 4/2024 | Clinger et al. |
| 2001/0049519 | A1 | 12/2001 | Holman et al. |
| 2002/0072705 | A1 | 6/2002 | Vrba et al. |
| 2002/0165569 | A1 | 11/2002 | Ramzipoor et al. |
| 2002/0183786 | A1 | 12/2002 | Girton |
| 2003/0009208 | A1 | 1/2003 | Snyder et al. |
| 2003/0093094 | A1 | 5/2003 | Diaz et al. |
| 2003/0181942 | A1 | 9/2003 | Sutton et al. |
| 2004/0034363 | A1 | 2/2004 | Wilson et al. |
| 2004/0059367 | A1 | 3/2004 | Davis et al. |
| 2004/0087964 | A1 | 5/2004 | Diaz et al. |
| 2006/0025801 | A1 | 2/2006 | Lulo et al. |
| 2006/0064151 | A1 | 3/2006 | Guterman |
| 2006/0100687 | A1 | 5/2006 | Fahey et al. |
| 2006/0116711 | A1 | 6/2006 | Elliott et al. |
| 2006/0116714 | A1 | 6/2006 | Sepetka et al. |
| 2006/0135986 | A1 | 6/2006 | Wallace et al. |
| 2006/0206139 | A1 | 9/2006 | Tekulve |
| 2006/0241685 | A1 | 10/2006 | Wilson et al. |
| 2006/0247677 | A1 | 11/2006 | Cheng et al. |
| 2006/0276824 | A1 | 12/2006 | Mitelberg et al. |
| 2006/0276825 | A1 | 12/2006 | Mitelberg et al. |
| 2006/0276826 | A1 | 12/2006 | Mitelberg et al. |
| 2006/0276827 | A1 | 12/2006 | Mitelberg et al. |
| 2006/0276830 | A1 | 12/2006 | Balgobin et al. |
| 2006/0276833 | A1 | 12/2006 | Balgobin et al. |
| 2007/0010850 | A1 | 1/2007 | Balgobin et al. |
| 2007/0055302 | A1 | 3/2007 | Henry et al. |
| 2007/0083132 | A1 | 4/2007 | Sharrow |
| 2007/0203519 | A1 | 8/2007 | Lorenzo et al. |
| 2007/0233168 | A1 | 10/2007 | Davis et al. |
| 2007/0270903 | A1 | 11/2007 | Davis, III et al. |
| 2008/0027561 | A1 | 1/2008 | Mitelberg et al. |
| 2008/0045997 | A1 | 2/2008 | Balgobin et al. |
| 2008/0097462 | A1 | 4/2008 | Mitelberg et al. |
| 2008/0119887 | A1 | 5/2008 | Que et al. |
| 2008/0269719 | A1 | 10/2008 | Balgobin et al. |
| 2008/0269721 | A1 | 10/2008 | Balgobin et al. |
| 2008/0281350 | A1 | 11/2008 | Sepetka |
| 2008/0300616 | A1 | 12/2008 | Que et al. |
| 2008/0306503 | A1 | 12/2008 | Que et al. |
| 2009/0062726 | A1 | 3/2009 | Ford et al. |
| 2009/0099592 | A1 | 4/2009 | Buiser et al. |
| 2009/0270877 | A1 | 10/2009 | Johnson et al. |
| 2009/0312748 | A1 | 12/2009 | Johnson et al. |
| 2010/0094395 | A1 | 4/2010 | Kellett |
| 2010/0114017 | A1 | 5/2010 | Lenker et al. |

(56) References Cited

U.S. PATENT DOCUMENTS

| | | | |
|---|---|---|---|
| 2010/0206453 | A1 | 8/2010 | Leeflang et al. |
| 2010/0324649 | A1 | 12/2010 | Mattsson |
| 2011/0092997 | A1 | 4/2011 | Kang |
| 2011/0118772 | A1 | 5/2011 | Chen et al. |
| 2011/0118776 | A1 | 5/2011 | Chen et al. |
| 2011/0202085 | A1 | 8/2011 | Loganathan et al. |
| 2011/0295303 | A1 | 12/2011 | Freudenthal |
| 2012/0035707 | A1 | 2/2012 | Mitelberg et al. |
| 2012/0041472 | A1 | 2/2012 | Tan et al. |
| 2012/0083868 | A1 | 4/2012 | Shrivastava et al. |
| 2012/0172913 | A1 | 7/2012 | Kurrus et al. |
| 2012/0172921 | A1 | 7/2012 | Yamanaka et al. |
| 2012/0179194 | A1 | 7/2012 | Wilson et al. |
| 2012/0283768 | A1 | 11/2012 | Cox et al. |
| 2012/0289772 | A1 | 11/2012 | O'Connell et al. |
| 2013/0066413 | A1 | 3/2013 | Jin et al. |
| 2013/0296915 | A1 | 11/2013 | Bodewadt |
| 2013/0325054 | A1 | 12/2013 | Watson |
| 2013/0338678 | A1 | 12/2013 | Loushin et al. |
| 2014/0058435 | A1 | 2/2014 | Jones et al. |
| 2014/0088565 | A1 | 3/2014 | Vongphakdy et al. |
| 2014/0135812 | A1 | 5/2014 | Divino et al. |
| 2014/0200607 | A1 | 7/2014 | Sepetka et al. |
| 2014/0207175 | A1 | 7/2014 | Aggerholm |
| 2014/0243883 | A1 | 8/2014 | Tsukashima et al. |
| 2014/0277078 | A1 | 9/2014 | Slazas et al. |
| 2014/0277084 | A1 | 9/2014 | Mirigian et al. |
| 2014/0277085 | A1 | 9/2014 | Mirigian et al. |
| 2014/0277092 | A1 | 9/2014 | Teoh et al. |
| 2014/0277093 | A1 | 9/2014 | Guo et al. |
| 2014/0277100 | A1 | 9/2014 | Kang |
| 2015/0005808 | A1 | 1/2015 | Chouinard et al. |
| 2015/0025562 | A1 | 1/2015 | Dinh et al. |
| 2015/0119884 | A1 | 4/2015 | Fung et al. |
| 2015/0164666 | A1 | 6/2015 | Johnson et al. |
| 2015/0182227 | A1 | 7/2015 | Le et al. |
| 2015/0230802 | A1 | 8/2015 | Lagodzki et al. |
| 2015/0335333 | A1 | 11/2015 | Jones et al. |
| 2016/0008003 | A1 | 1/2016 | Kleshinski et al. |
| 2016/0022275 | A1 | 1/2016 | Garza |
| 2016/0022445 | A1 | 1/2016 | Ruvalacaba et al. |
| 2016/0045347 | A1 | 2/2016 | Smouse et al. |
| 2016/0157869 | A1 | 6/2016 | Elgård et al. |
| 2016/0228125 | A1 | 8/2016 | Pederson, Jr. et al. |
| 2016/0278782 | A1 | 9/2016 | Anderson et al. |
| 2016/0310304 | A1 | 10/2016 | Mialhe |
| 2016/0331383 | A1 | 11/2016 | Hebert et al. |
| 2016/0346508 | A1 | 12/2016 | Williams et al. |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072165 | A1 | 3/2017 | Lim et al. |
| 2017/0072452 | A1 | 3/2017 | Monetti et al. |
| 2017/0079671 | A1 | 3/2017 | Morero |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095258 | A1 | 4/2017 | Tassoni et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Granfield |
| 2017/0100183 | A1 | 4/2017 | Iaizzo et al. |
| 2017/0105739 | A1 | 4/2017 | Dias et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |
| 2017/0231749 | A1 | 8/2017 | Perkins et al. |
| 2017/0245864 | A1 | 8/2017 | Franano et al. |
| 2017/0245885 | A1 | 8/2017 | Lenker |
| 2017/0252064 | A1 | 9/2017 | Staunton |
| 2017/0258476 | A1 | 9/2017 | Hayakawa et al. |
| 2017/0265983 | A1 | 9/2017 | Lam et al. |
| 2017/0281192 | A1 | 10/2017 | Tieu et al. |
| 2017/0281331 | A1 | 10/2017 | Perkins et al. |
| 2017/0281344 | A1 | 10/2017 | Costello |
| 2017/0281909 | A1 | 10/2017 | Northrop et al. |
| 2017/0281912 | A1 | 10/2017 | Melder et al. |
| 2017/0290593 | A1 | 10/2017 | Cruise et al. |
| 2017/0290654 | A1 | 10/2017 | Sethna |
| 2017/0296324 | A1 | 10/2017 | Argentine |
| 2017/0296325 | A1 | 10/2017 | Marrocco et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0304041 | A1 | 10/2017 | Argentine |
| 2017/0304097 | A1 | 10/2017 | Corwin et al. |
| 2017/0304595 | A1 | 10/2017 | Nagasrinivasa et al. |
| 2017/0312109 | A1 | 11/2017 | Le |
| 2017/0312484 | A1 | 11/2017 | Shipley et al. |
| 2017/0316561 | A1 | 11/2017 | Helm et al. |
| 2017/0319826 | A1 | 11/2017 | Bowman et al. |
| 2017/0333228 | A1 | 11/2017 | Orth et al. |
| 2017/0333236 | A1 | 11/2017 | Greenan |
| 2017/0333678 | A1 | 11/2017 | Bowman et al. |
| 2017/0340383 | A1 | 11/2017 | Bloom et al. |
| 2017/0348014 | A1 | 12/2017 | Wallace et al. |
| 2017/0348514 | A1 | 12/2017 | Guyon et al. |
| 2017/0367712 | A1 | 12/2017 | Johnson et al. |
| 2018/0028779 | A1 | 2/2018 | von Oepen et al. |
| 2018/0036508 | A1 | 2/2018 | Ozasa et al. |
| 2018/0078263 | A1 | 3/2018 | Stoppenhagen et al. |
| 2018/0228493 | A1 | 8/2018 | Aguilar et al. |
| 2018/0250150 | A1 | 9/2018 | Majercak et al. |
| 2018/0280667 | A1 | 10/2018 | Keren |
| 2018/0289375 | A1 | 10/2018 | Hebert et al. |
| 2018/0296222 | A1 | 10/2018 | Hebert et al. |
| 2018/0325706 | A1 | 11/2018 | Hebert et al. |
| 2019/0142565 | A1 | 5/2019 | Follmer et al. |
| 2019/0159784 | A1 | 5/2019 | Sananes et al. |
| 2019/0192162 | A1 | 6/2019 | Lorenzo et al. |
| 2019/0201688 | A1 | 7/2019 | Olson |
| 2019/0231566 | A1 | 8/2019 | Tassoni et al. |
| 2019/0255290 | A1 | 8/2019 | Snyder et al. |
| 2019/0314033 | A1 | 10/2019 | Mirigian et al. |
| 2019/0328398 | A1 | 10/2019 | Lorenzo |
| 2020/0015876 | A1 | 1/2020 | Chou et al. |
| 2020/0078024 | A1 | 3/2020 | Tekulve |
| 2020/0138448 | A1 | 5/2020 | Dasnurkar et al. |
| 2020/0147347 | A1 | 5/2020 | Cottone |
| 2020/0187951 | A1 | 6/2020 | Blumenstyk |
| 2020/0229957 | A1 | 7/2020 | Bardsley et al. |
| 2020/0397444 | A1 | 12/2020 | Montidoro et al. |

(56) References Cited

U.S. PATENT DOCUMENTS

| | | | |
|---|---|---|---|
| 2020/0406048 | A1 | 12/2020 | Rentas Torres et al. |
| 2021/0001082 | A1 | 1/2021 | Lorenzo et al. |
| 2021/0045759 | A1 | 2/2021 | Merhi et al. |
| 2021/0085498 | A1 | 3/2021 | Nygaard et al. |
| 2021/0186513 | A1 | 6/2021 | Hoshino et al. |
| 2021/0196281 | A1 | 7/2021 | Blumenstyk et al. |
| 2021/0213252 | A1 | 7/2021 | Lorenzo et al. |
| 2021/0220013 | A1 | 7/2021 | Libarnes et al. |
| 2021/0338248 | A1 | 11/2021 | Lorenzo et al. |
| 2021/0346002 | A1 | 11/2021 | Lorenzo et al. |
| 2021/0353299 | A1 | 11/2021 | Hamel et al. |

FOREIGN PATENT DOCUMENTS

| | | | |
|---|---|---|---|
| CN | 104203341 | | 12/2014 |
| CN | 106456422 | A | 2/2017 |
| CN | 109770985 | A | 5/2019 |
| EP | 1985244 | A2 | 10/2008 |
| EP | 2498691 | A0 | 9/2012 |
| EP | 3092956 | A1 | 11/2016 |
| EP | 3501427 | A1 | 6/2019 |
| EP | 3795097 | A1 | 3/2021 |
| EP | 3799803 | A1 | 4/2021 |
| EP | 3854321 | A1 | 7/2021 |
| EP | 1188414 | A1 | 3/2022 |
| EP | 4119065 | A1 | 1/2023 |
| JP | H10-507090 | A | 7/1998 |
| JP | 2006-334408 | A | 12/2006 |
| JP | 2006346350 | A | 12/2006 |
| JP | 2012-523943 | A | 10/2012 |
| JP | 2013-78584 | A | 5/2013 |
| JP | 2014-399 | A | 1/2014 |
| JP | 2016-179174 | A | 10/2016 |
| JP | 2017-529894 | A | 10/2017 |
| WO | WO 2007/070793 | A2 | 6/2007 |
| WO | WO 2008/064209 | A1 | 5/2008 |
| WO | WO 2009/132045 | A2 | 10/2009 |
| WO | WO 2012/158152 | A1 | 11/2012 |
| WO | WO 2016/014985 | A1 | 1/2016 |
| WO | WO 2017/066386 | A1 | 4/2017 |
| WO | WO 2018/022186 | A1 | 2/2018 |
| WO | WO 2020/148768 | A1 | 7/2020 |

HOOK WIRE FOR PREVENTING PREMATURE EMBOLIC IMPLANT DETACHMENT

CROSS REFERENCE TO RELATED APPLICATION

The present application is a continuation application of U.S. patent application Ser. No. 17/685,147 filed Mar. 2, 2022. The entire contents of which are hereby incorporated by reference.

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a “pull wire”.

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the “pull wire” and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Various systems and methods of delivering an implant to a target location of a body vessel are disclosed. A detachment system can include a tubular body including a lumen extending therethrough and a distal tube on a distal end of the tubular body. A loop wire can be affixed at a first end to the tubular body and can include a loop opening positioned approximate a distal end of the distal tube. A pull wire can extend through the lumen. A hook wire can extend radially through a sidewall of the distal tube and into the lumen. The hook wire can be positioned around a pull wire portion and tensioned such that the pull wire portion abuts the distal tube and provides frictional resistance between the pull wire portion and the sidewall of the distal tube. The frictional resistance can be effective to inhibit premature detachment of the implant.

In one aspect, a detachment system for delivering an implantable medical device to a target location of a body vessel is disclosed. The detachment system can include a tubular body that includes a lumen extending therethrough and a distal tube that is disposed on a distal end of the tubular body. The detachment system can include a loop wire that includes a first end affixed to the tubular body and including a loop opening positioned approximate a distal end of the distal tube. The detachment system can include a pull wire extending through the lumen. The detachment system can include a hook wire that extends radially through a sidewall of the distal tube and into the lumen. The hook wire can be positioned around a pull wire portion of the pull wire and tensioned such that the pull wire portion abuts the distal tube to thereby provide frictional resistance between the pull wire portion and the sidewall of the distal tube. The loop wire and the pull wire can be positioned to secure the implantable medical device to the delivery system. The frictional resistance provided by the pull wire portion against the tubular body is effective to inhibit premature detachment of the implantable medical device as the implantable medical device is delivered by the detachment system to the target location of the body vessel.

In some embodiments, the hook wire includes hook wire ends that are welded to the distal tube. In some embodiments, the distal tube includes laser cut port holes in the sidewall. The hook wire can extend radially through each of the port holes and into the lumen of the distal tube. In some embodiments, the detachment system can include a laser cut window in the distal tube positioned opposite the laser cut port holes.

In some embodiments, the frictional resistance provided by the pull wire portion can be a force between approximately 5 gram-force and 25 gram-force.

In some embodiments, the loop wire and the pull wire are movable to release the implantable medical device from the detachment system.

In some embodiments, the hook wire can be stretch resistant.

In some embodiments, the pull wire can include a polytetrafluoroethylene (PTFE) coating.

In some embodiments, the distal tube includes a compressed distal portion and the loop opening is positioned approximate a distal end of the compressed distal portion.

In some embodiments, the loop wire is stretch resistant and the loop wire is under tension when the implantable medical device is secured to the detachment system.

In some embodiments, the tubular body includes a support coil that is disposed in a proximal direction from the distal tube.

In some embodiments, the hook wire includes a hook wire portion within the lumen of the distal tube and extending longitudinally along a longitudinal axis of the distal tube.

In another aspect, a method of using a detachment system is disclosed. The method can include providing a tubular body that includes a lumen extending therethrough and a distal tube disposed on a distal end of the tubular body. The method can include affixing a loop wire to the distal tube and positioning a loop opening in the loop wire approximate a distal end of the distal tube while the loop wire is affixed to the distal tube such that the loop wire is extended through the lumen. The method can include extending a pull wire through the lumen. The method can include extending the loop opening through a locking portion of an implantable medical device. The method can include extending a distal end of the pull wire through the loop opening. The method can include extending a hook wire radially through a sidewall of the distal tube and into the lumen. The method can include positioning the hook wire around a pull wire portion of the pull wire. The method can include tensioning the hook wire such that the pull wire portion abuts the sidewall to thereby provide frictional resistance against the distal tube. The method can include preventing, through frictional resistance of the pull wire portion against the distal tube, release of the implantable medical device while the implantable medical device is delivered through vasculature to a treatment site.

In some embodiments, the method can include providing a force sufficient to overcome the frictional resistance of the pull wire portion against the sidewall to thereby translate the pull wire proximally and release the implantable medical device at the treatment site.

In some embodiments, the method can include tensioning the pull wire portion against the sidewall with the hook wire to provide frictional resistance between approximately 5 gram-force and 25 gram-force.

In some embodiments, the method can include welding respective ends of the hook wire to the distal tube.

In some embodiments, extending a hook wire through the distal tube can include forming port holes through the sidewall and extending the hook wire radially through each of the port holes and into the lumen of the distal tube.

In some embodiments, the method can include forming a laser cut window in the distal tube positioned opposite the laser cut port holes.

In some embodiments, the distal tube can include a compressible distal portion such that the loop opening is approximate a distal end of the compressible distal portion, and the method further includes compressing the compressible distal portion.

In some embodiments, positioning the hook wire around a pull wire portion of the pull wire can include positioning a hook wire portion within the lumen of the tubular body that extends longitudinally along a longitudinal axis of the distal tube.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figures 1, 2A, 2B, 2C, 2D, 2E:
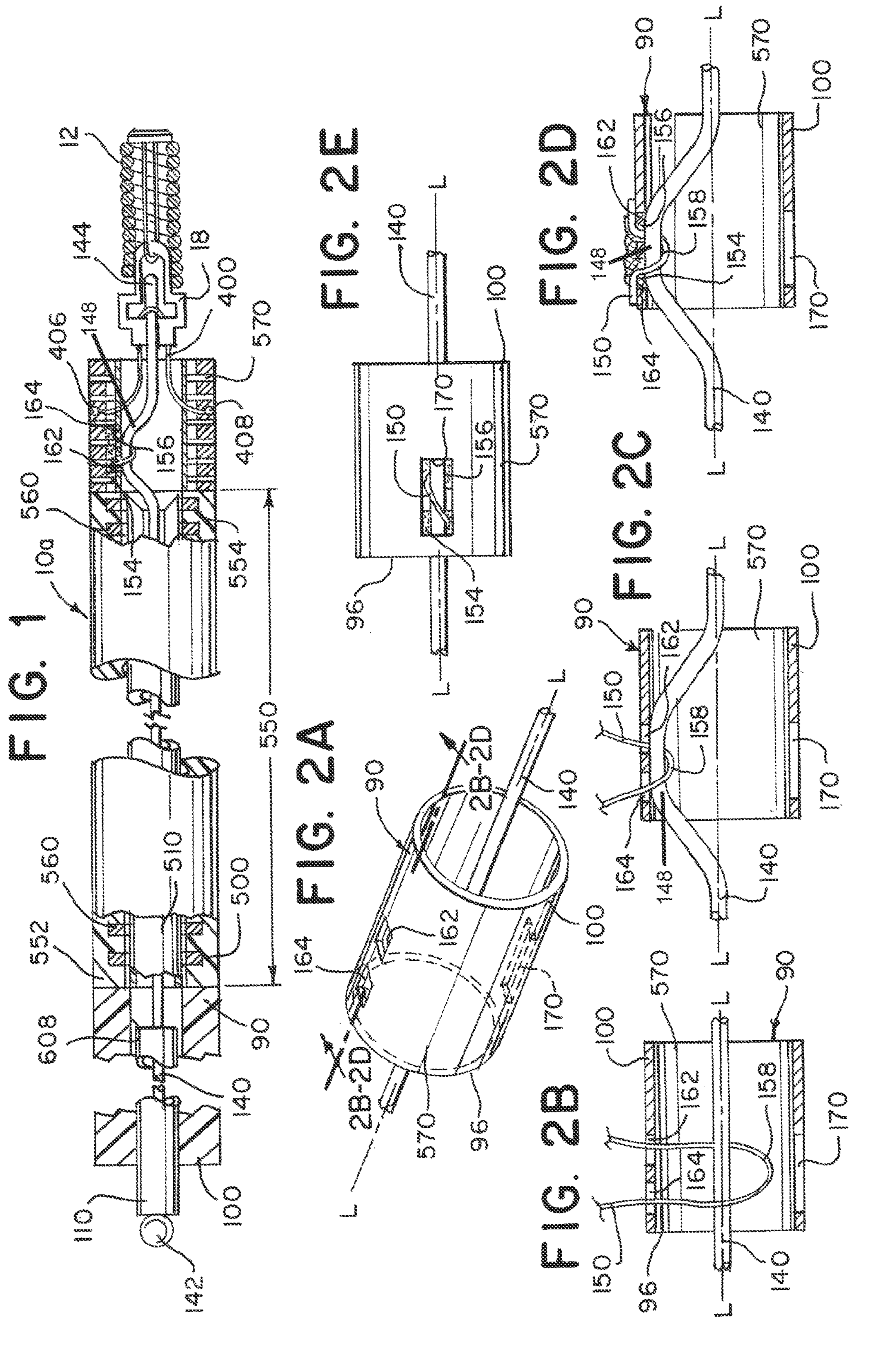
FIG. 1 an illustration of a detachment system and implant, according to aspects of the present invention.
FIGS. 2A-2E are illustrations of the process of inserting a hook wire into a lumen of a detachment system, positioning the hook wire around a pull wire portion, and tensioning the hook wire to cause the pull wire portion to abut a sidewall of the detachment system, according to aspects of the present invention.

Turning to the figures, FIG. 1 shows an example detachment system 10 for deploying an implantable medical device 12 to a target location of a body vessel. The example detachment system 10 can include a proximal tube 100, a support coil 550 positioned distal to the proximal tube 100, and a distal tube 570 positioned distal to the support coil 550. The proximal tube 100, support coil 550, and distal tube 570 may collectively have a lumen 608 extending therethrough. That is, lumen 608 extends from a proximal end of proximal tube 100, through support coil 550, and through distal tube 570. Implant 12 can be positioned distal to the distal tube 570. Positioned within the lumen 608 of the support coil 550 can be an inner support tube 510. Inner support tube 510 can be welded or otherwise attached to the inner sidewall of support coil 550. Inner support tube 510 can provide structural support to the support coil 550. Support coil can additionally be characterized by interference cuts from the sidewall of the support coil 550. A sleeve 500 can surround the coiled section. A pull wire 140 can extend through the lumen 608 of delivery system 10. Within lumen 608 of proximal tube 100 can be positioned a proximal support tube 110. Proximal support tube can be welded or otherwise attached to the inner sidewall of proximal tube 100. The pull wire 140 can include a pull wire bead 142 located on a proximal end of pull wire 140. The pull wire bead 142 can be sized such that the pull wire bead 142 is larger than the space between the proximal support tube 110 such that the pull wire bead 142 interferes with the proximal support tube 110 and proximal support tube 110 retains the pull wire bead 142 proximal to the proximal tube 100.

Located at a proximal end of distal tube 570 can be a plurality of port holes 162, 164 that are laser cut in the sidewall 96 of distal tube 570. A hook wire 150 can be positioned radially into the lumen orthogonal to a longitudinal axis defined by the delivery system 10 through the port holes 162, 164. The hook wire 150 can be positioned around a pull wire portion 148 of pull wire 140. Respective ends 154, 156 of the hook wire 150 can be attached to the sidewall 96 of distal tube 570 at the respective port holes 162, 164 using any method known in the pertinent art. For example, hook wire ends 154, 156 of hook wire 150 can be welded to the sidewall 96 at port holes 162, 164. Hook wire 150 can be tensioned such that a pull wire portion 148 is pulled into contact and abuts sidewall 96 of distal tube 570. The pull wire portion 148 can provide a frictional resistance to proximal translation of the pull wire 140 as the detachment system 10 navigates tortuous vasculature to a treatment site. According to some embodiments, a laser cut window 170 may be formed in the sidewall 96 of distal tube 570 opposite to the port holes 162, 164.

A loop wire opening 405 of loop wire 400 can be located at a distal portion 404 of loop wire 400 and can extend through a locking member 18 of implant 12. The distal end 144 of pull wire 140 can be positioned through the loop wire opening 405 of loop wire 400 to secure implant 12 to the delivery system 10. The proximal ends 406, 408 of loop wire 400 can be attached to the sidewall 96 of the distal tube 570. The attachment can be of any kind known in the pertinent art, including but not limited to welding proximal ends 406, 408 to the distal tube 570 sidewall 96 and/or gluing proximal ends 406, 408 to the distal tube. The loop wire 400 can be effective to hold the compressible distal section 300 of distal tube 570 in compression until implant 12 is released from the detachment system 10.

When the delivery system 10 is assembled, the support coil 550 and sleeve 500 can be more flexible than the distal tube 570 and the proximal tube 100. One way to measure flexibility is to perform a three-point bend test wherein a portion of the delivery system 10 is held fixed at two end points, a force is applied perpendicularly to the delivery system 10 centrally between the points, and flexibility is quantified by the length of deflection of the delivery system 10 caused by the force. When measured in this way, in some examples, the support coil 550 and sleeve 500 can be about 1.5 times more flexible than the distal tube 570 and about 20 times more flexible than the proximal tube 100. That is, when the three-point test is performed identically on the three sections 100, 550, and 570, the coiled section deflect over a length that is about 1.5 times the deflection of the distal tube 570 and about 20 times the length of deflection of the proximal tube 100. Flexibility can be measured in other ways as would be appreciated and understood by a person having pertinent skill in the requisite art. When the detachment system 10 is assembled, the support coil 550 and sleeve 500 can be more flexible than the distal tube 570 and the proximal tube 100 as flexibility is determined by other means as would be known to a person of ordinary skill in the art.

According to some embodiments, the distal tube 570 can include a compressible distal portion 300, which can be compressed and formed from a spiral-cut portion of the distal tube 570, formed by a laser cutting operation. Additionally, or alternatively, the compressible distal portion 300 can be formed of a wound wire, spiral ribbon, or other arrangement allowing axial adjustment according to the present invention. Preferably, compressible distal portion 300 is in the elongated condition at rest and automatically or resiliently returns to the elongated condition from a compressed condition, unless otherwise constrained. In some embodiments, the loop wire 400 is effective to hold the compressed distal portion 300 in compression while the implant 12 is delivered to the treatment site.

Pull wire 140 can be constructed out of any suitable material, for example, pull wire 140 can be constructed of stainless steel or memory shape material, such as nitinol. According to some embodiments, pull wire 140 can additionally be coated with polytetrafluoroethylene (PTFE). According to some embodiments, a PTFE coating can be selectively removed from the pull wire portion 148 to increase frictional resistance that the pull wire portion 148 provides against sidewall 96.

FIGS. 2A-2E are illustrations of the process of inserting a hook wire into a lumen of a detachment system, positioning the hook wire around a pull wire portion, and tensioning the hook wire to cause the pull wire portion to abut a sidewall of the detachment system, according to aspects of the present invention. As shown in FIG. 2A, hook wire 150 can be positioned orthogonal to the longitudinal axis L-L defined by the tubular body 90 of detachment system 10. The hook wire 150 can be positioned radially into lumen 608 through laser cut window 170. As shown in FIG. 1A, hook wire 150 can be positioned around a pull wire portion 148 of pull wire 140. Respective ends 154, 156 of hook wire 150 can extend through port holes 162, 164, as shown in FIG. 2B. FIG. 2C shows the hook wire 150 pulled tightly against the pull wire portion 148 of pull wire 140 such that pull wire portion 148 abuts the sidewall 96 of distal tube 570. A hook wire portion 158 of hook wire 150 can be seen positioned within the lumen 608 of tubular body 90 such that the hook wire portion 158 extends along longitudinal axis L-L while a remainder of the hook wire portion 150 is approximately orthogonal to the longitudinal axis L-L. In FIG. 2D, respective ends 154, 156 of hook wire 150 are welded, glued, or otherwise attached to the sidewall 96 of distal tube 570 using any method known in the pertinent art. Hook wire ends 154, 156 can be seen attached by welds in FIG. 2D approximate the port holes 162, 164 within sidewall 96. FIG. 2E shows the positioned of pull wire portion 148 against sidewall 96 as can be seen through laser cut window 170 that is positioned opposite port holes 162, 164.

Figure 3:
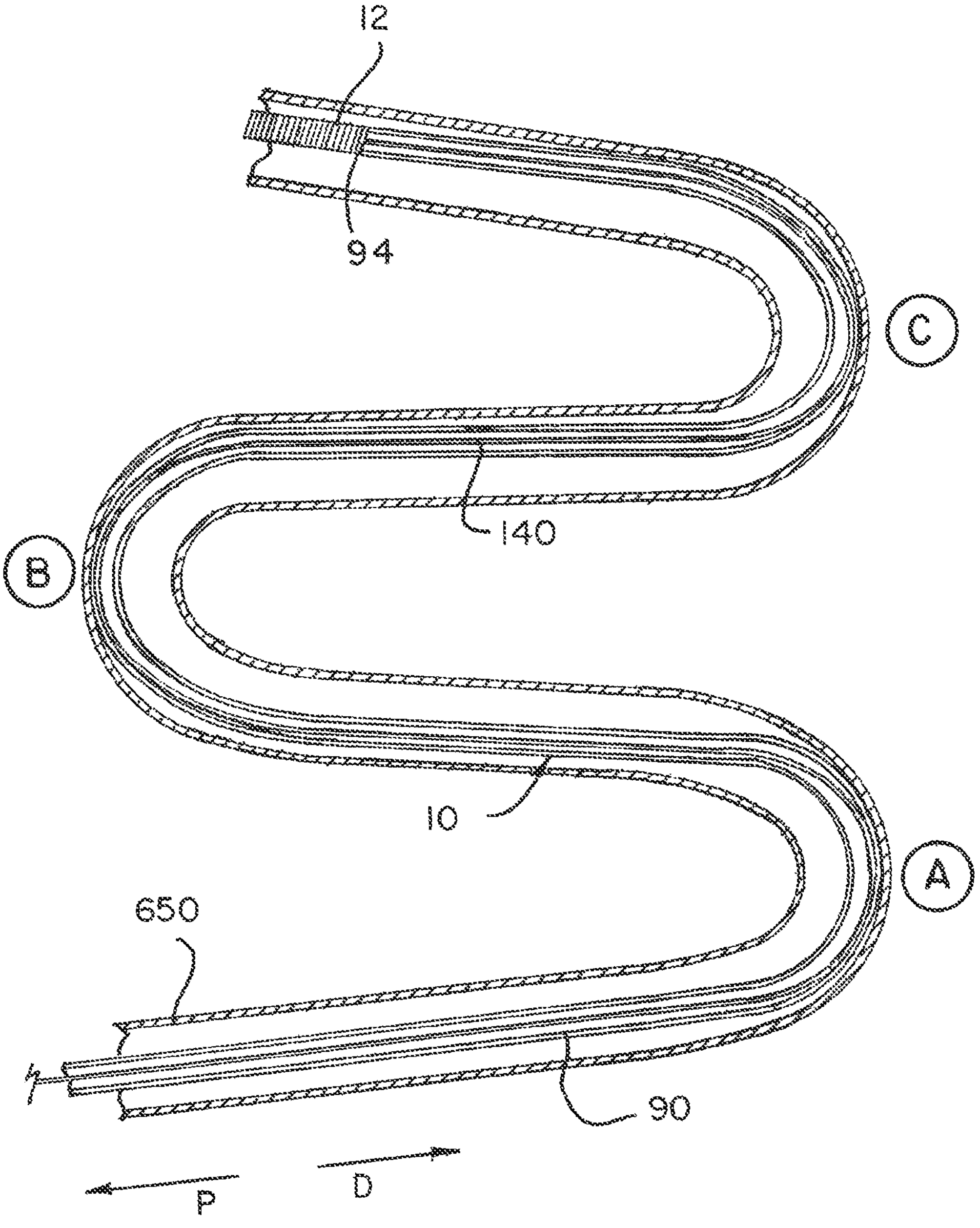
FIG. 3 is an illustration of a delivery system navigating a body lumen according to aspects of the present invention.

FIG. 3 illustrates positioning of an implant 12 such as an embolic coil suitable for aneurysm treatment, a guide catheter 650, and a delivery system 10 including a tubular body 90 and a pull wire 140 within tortuous vasculature (vasculature not illustrated). At bends A, B, and C, the tubular body 90 can extend to a sidewall of the guide catheter 650 on each outer curve of each bend, and likewise, the pull wire 140 can extend to a sidewall of the tubular body 90 on each outer curve of each bend. During a procedure, the tubular body 90 and pull wire 140 can be fed into the guide catheter 650 in the distal direction D, first passing through bend A, then bend B, and then bend C. As the tubular body 90 and pull wire 140 navigate the bends, the pull wire 140 is prevented from translating proximally with respect to the tubular body. The frictional resistance caused by the pull wire portion 148 held against sidewall 96 of distal tube 570 provides a resistance to the proximal drift that the pull wire 140 can otherwise experience while the detachment system is delivered through the tortuous vasculature to a treatment site. As pull wire 140 is "pulled" proximally during navigation of the vasculature, this force is resisted and balanced by the frictional resistance caused by the tensioned hook wire 150 holding pull wire portion 148 tightly against the sidewall 96 of distal tube 570. The amount of frictional resistance provided by the pull wire portion 148 can be varied as would be understood by a person having pertinent skill in the art, by varying the size of pull wire 140, varying the materials of pull wire 140, varying the size of pull wire portion 148, varying the tension of hook wire 150 against pull wire portion 148, and/or adding or selectively removing a coating of pull wire 140, such as polytetrafluoroethylene (PTFE).

Figure 4:
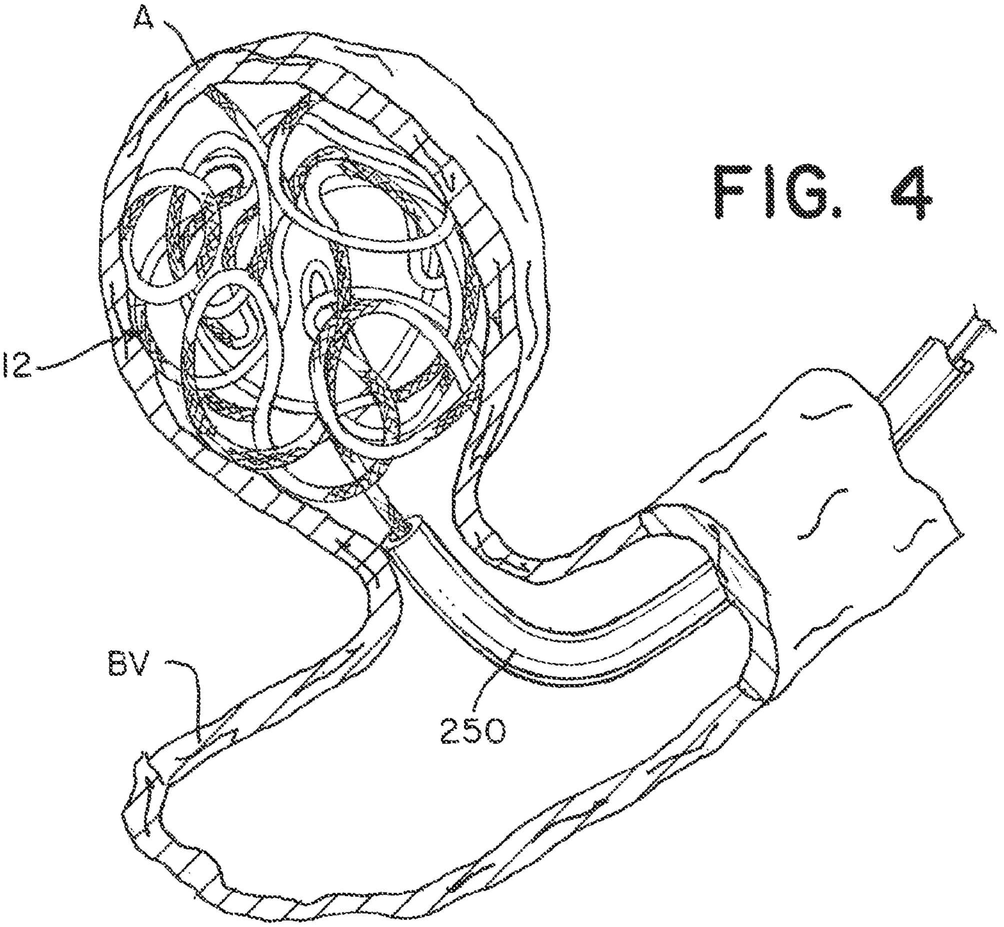
FIG. 4 is an illustration of embolic coils being positioned within an aneurysm according to aspects of the present invention.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

Figure 5A:
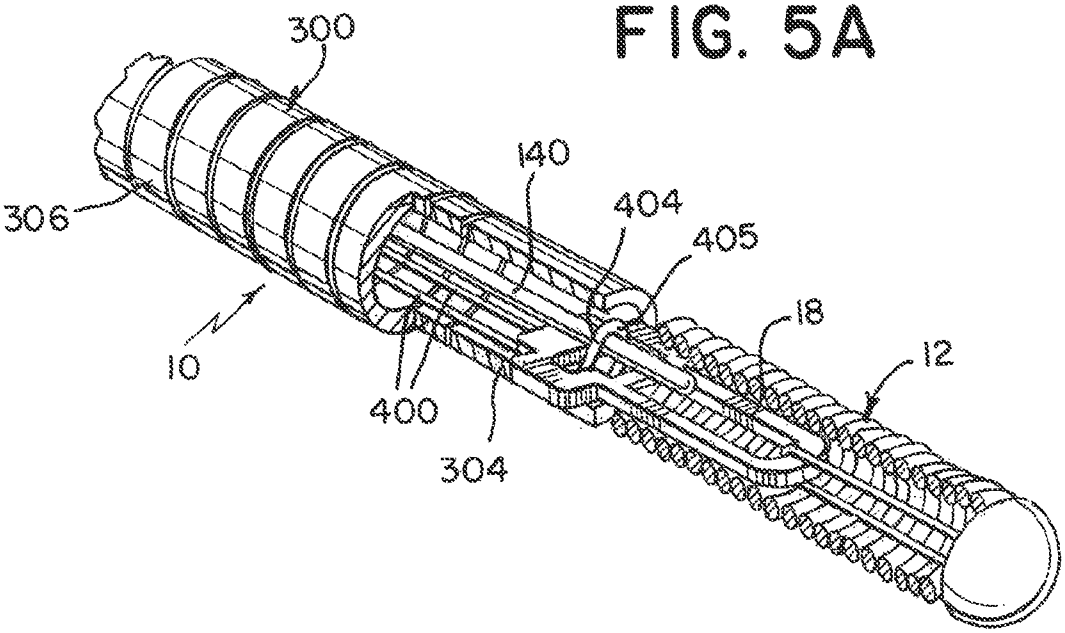
FIGS. 5A-5D illustrate a sequence of steps for releasing an embolic implant from the delivery member, according to aspects of the present invention.
Figure 5B:
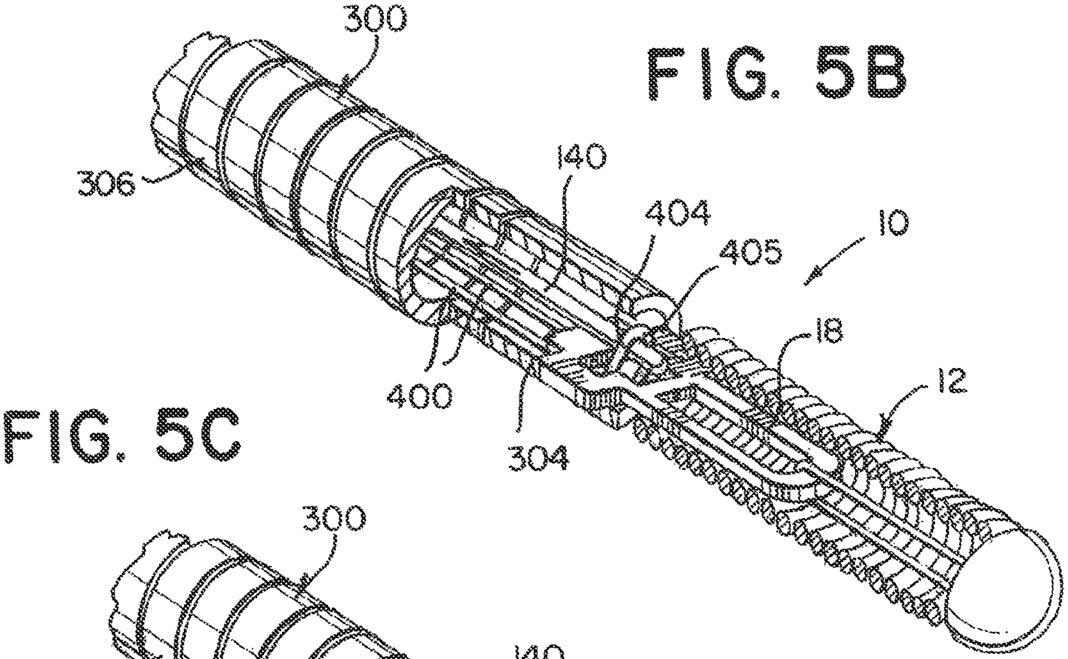
Figure 5C:
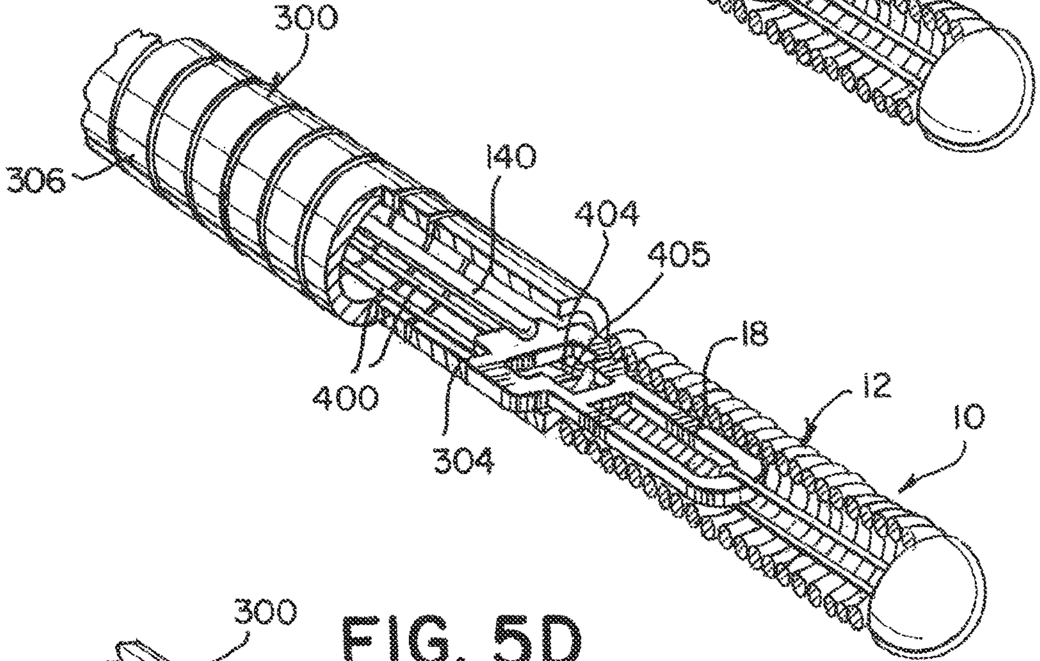
Figure 5D:
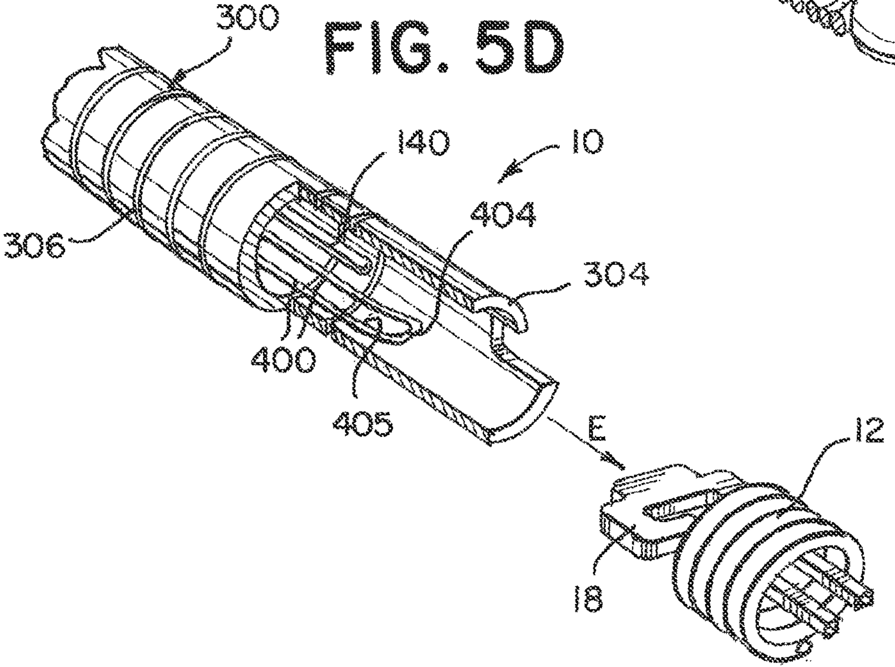

FIGS. 5A-5D illustrate a time sequence of steps for releasing an embolic implant 12 from a delivery system 10. The detachment system 10 can be configured such as illustrated in the previous figures and as otherwise described herein. FIG. 5A illustrates an engagement system including the loop wire 400 and pull wire 140 locked into a locking portion 18 of the medical device 12. The spiral cuts 306 of the compressible distal portion 300 can be compressed and the loop wire opening 405 at a distal end 404 of the loop wire 400 can be placed through the locking portion 18. When the pull wire 140 is put through the loop wire opening 405 the medical device 12 is now secure. FIG. 5B illustrates the pull wire 140 being drawn proximally to begin the release sequence for the medical device 12. FIG. 5C illustrates the instant the distal end 144 of the pull wire exits the loop wire opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 5D illustrates the end of the release sequence. Here, the compressible portion 300 has extended/returned to its original shape and "sprung" forward. An elastic force E is imparted by the distal end 305 of the compressible distal portion 300 to the medical device 12 to "push" it away to ensure a clean separation and delivery of the medical device 12.

The compressible portion 300 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the compressible distal portion 300.

Figure 6:
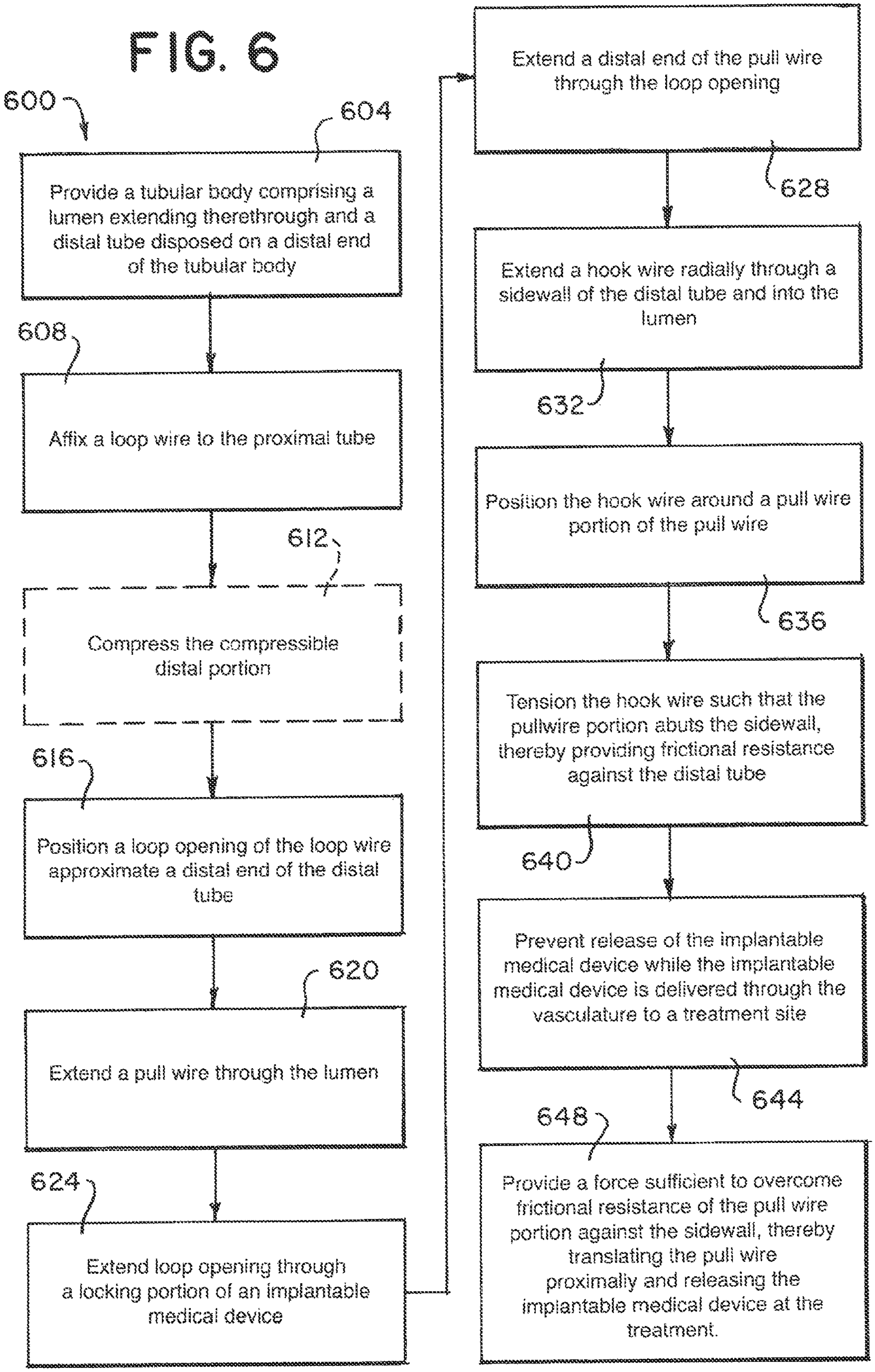
FIG. 6 is a flowchart of an example method of using the detachment system, according to aspects of the present invention.

FIG. 6 is a flowchart of an example method of using the detachment system, according to aspects of the present invention. In block 604, the method can include providing a tubular body 90. The tubular body can include a lumen 608 extending therethrough and a distal tube 570 disposed on a distal end 94 of the tubular body 90. In some embodiments, the distal tube 570 can include a compressible distal section 300 characterized by spiral cuts 306 made within the distal tube 570. In block 608, the method can include affixing a loop wire 400 to the distal tube 570. Loop wire ends 406, 408 of loop wire 400 can be affixed to the distal tube 570 as shown in FIG. 1.

In optional block 612, the distal tube 570 can include a compressible distal portion 300 such that the loop wire opening 405 is approximate a distal end 304 of the compressible distal portion. The method can include compressing the compressible distal portion 300 of the distal tube 570.

In block 616, the method can include positioning a loop wire opening 405 of the loop wire 400 approximate a distal end of the distal tube 570 while the loop wire is affixed to the distal tube 570 such that the loop wire is extended through the lumen 608. In block 620, a pull wire 140 can be extended through the lumen 608. In block 624, the method can include extending a loop wire opening 405 through a locking portion 18 of an implantable medical device 12. In block 628, the method can include extending a distal end 144 of the pull wire 140 through the loop opening. In this configuration, the implantable medical device 12 is secured to the detachment system 10. In block 632, the method can include extending a hook wire 150 radially through a sidewall 96 of the distal tube 570 and into the lumen 608. In block 636, the hook wire 150 can be positioned around a pull wire portion 148 of the pull wire 140. In block 640, the hook wire 150 can be tensioned such that the pull wire portion 148 abuts the sidewall 96 of distal tube 570. The pull wire portion 148 can provide a frictional resistance against the distal tube as the hook wire 150 holds the pull wire portion 148 under tension against the sidewall 96.

In block 644, the method can include preventing the release of the implantable medical device 12 while the implantable medical device 12 is delivered through vasculature to a treatment site. For example, as shown in FIG. 3, the detachment system 10 and implant implantable medical device 12 can travel through tortuous vasculature through bends A, B, C. As the detachment system moves around example bends A, B, C, pull wire 140 can be prevented from translated proximally with respect to the tubular body 90 due to the frictional resistance of pull wire portion 148 against sidewall 96 of distal tube 570. In block 648, the method can include providing a force sufficient to overcome the frictional resistance of the pull wire portion 148 against the sidewall 96. The force can cause the pull wire 140 to be translated proximally, which allows distal end 144 to exit loop wire opening 405 of loop wire 140, thereby allowing the implantable medical device 12 to be released from the detachment system 10, for example, as shown in FIG. 5D.

In some embodiments, the method can include tensioning the pull wire portion 148 against the sidewall 96 with the hook wire 150 to provide frictional resistance between approximately 5 gram-force and 25 gram-force.

In some embodiments, the method can include welding respective ends 154, 156 of the hook wire 150 to the distal tube 570. In some embodiments, positioning the hook wire 150 around a pull wire portion 148 of the pull wire 140 can further include positioning a hook wire portion 158 within the lumen 608 of the distal tube 570 that extends longitudinally along a longitudinal axis L-L of the distal tube 570.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A detachment system for delivering an implantable medical device to a target location of a body vessel, the detachment system comprising:

a tubular body and a distal tube disposed on the end of the tubular body, wherein a lumen extends through the tubular body and the distal tube;

a loop wire comprising a first end affixed to the tubular body and comprising a loop opening positioned approximate a distal end of the distal tube;

a pull wire extending through the lumen;

a hook wire extending radially through a sidewall of the distal tube and into the lumen, the hook wire positioned around a pull wire portion of the pull wire and tensioned such that the pull wire portion abuts the distal tube;

wherein the loop wire and the pull wire are positioned to secure the implantable medical device to the detachment system.

2. The detachment system of claim 1, wherein the hook wire comprises hook wire ends that are welded to the distal tube.

3. The detachment system of claim 1, wherein the distal tube comprises laser cut port holes in the sidewall, the hook wire extending radially through each of the laser cut port holes and into the lumen.

4. The detachment system of claim 3, further comprising a laser cut window in the distal tube positioned opposite the laser cut port holes.

5. The detachment system of claim 1, wherein a frictional resistance provided by the pull wire portion comprises a force between approximately 5 gram-force and 25 gram-force.

6. The detachment system of claim 1, wherein the loop wire and the pull wire are movable to release the implantable medical device from the detachment system.

7. The detachment system of claim 1, wherein the hook wire is stretch resistant.

8. The detachment system of claim 1, wherein the pull wire comprises a polytetrafluoroethylene coating.

9. The detachment system of claim 1, wherein the distal tube comprises a compressed distal portion and the loop opening is positioned approximate a distal end of the compressed distal portion.

10. The detachment system of claim 1, wherein the loop wire is stretch resistant, and wherein the loop wire is under tension when the implantable medical device is secured to the detachment system.

11. The detachment system of claim 1, wherein the tubular body further comprises a support coil disposed in a proximal direction from the distal tube.

12. The detachment system of claim 11, wherein the hook wire comprises a hook wire portion positioned within the lumen and extending longitudinally along a longitudinal axis of the distal tube.

13. A method comprising:

providing a tubular body and a distal tube disposed on the end of the tubular body, wherein a lumen extends through the tubular body and the distal tube;

affixing a loop wire to the distal tube;

positioning a loop opening in the loop wire approximate a distal end of the distal tube while the loop wire is affixed to the distal tube such that the loop wire is extended through the lumen;

extending a pull wire through the lumen;

extending the loop opening through a locking portion of an implantable medical device;

extending a distal end of the pull wire through the loop opening;

extending a hook wire radially through a sidewall of the distal tube and into the lumen;

positioning the hook wire around a pull wire portion of the pull wire;

tensioning the hook wire such that the pull wire portion abuts the sidewall; and preventing release of the implantable medical device while the implantable medical device is delivered through vasculature to a treatment site.

14. The method of claim 13, further comprising:

providing a force sufficient to overcome a frictional resistance of the pull wire portion against the sidewall, thereby translating the pull wire proximally and releasing the implantable medical device at the treatment site.

15. The method of claim 13, further comprising:

tensioning the pull wire portion against the sidewall with the hook wire to provide a frictional resistance between approximately 5 gram-force and 25 gram-force.

16. The method of claim 13, further comprising welding respective ends of the hook wire to the distal tube.

17. The method of claim 13, wherein extending the hook wire radially through the distal tube further comprises forming port holes through the sidewall, the hook wire extending radially through each of the port holes and the lumen.

18. The method of claim 17, further comprising forming a laser cut window in the distal tube positioned opposite the port holes.

19. The method of claim 13, wherein the distal tube comprises a compressible distal portion such that the loop opening is approximate a distal end of the compressible distal portion, and the method further comprises compressing the compressible distal portion.

20. The method of claim 13, wherein positioning the hook wire around the pull wire portion of the pull wire further comprises positioning a hook wire portion within the lumen that extends longitudinally along a longitudinal axis of the distal tube.

* * * * *